United States Patent [19]

Fekete et al.

[11] E Re. 29,698

[45] Reissued Jul. 11, 1978

[54] STABILIZATION OF AHF USING HEPARIN

[75] Inventors: Lajos F. Fekete, Costa Mesa; Stephen L. Holst, Santa Ana, both of Calif.

[73] Assignee: Baxter Travenol Laboratories, Inc., Deerfield, Ill.

[21] Appl. No.: 674,270

[22] Filed: Apr. 6, 1976

Related U.S. Patent Documents

Reissue of:

[64] Patent No.: 3,803,115
Issued: Apr. 9, 1974
Appl. No.: 254,148
Filed: May 17, 1972

[51] Int. Cl.[2] ..... C07G 7/00

[52] U.S. Cl. ..... 260/112 B; 424/101; 424/177

[58] Field of Search ..... 260/112 B

[56] References Cited

U.S. PATENT DOCUMENTS

| | | | |
|---|---|---|---|
| 2,867,567 | 1/1959 | Bidwell | 260/112 B X |
| 3,560,475 | 2/1971 | Fekete et al. | 260/112 B |
| 3,631,018 | 12/1971 | Shanbrom et al. | 260/112 B |
| 3,652,530 | 3/1972 | Johnson et al. | 260/112 B |
| 3,682,881 | 8/1972 | Fekete et al. | 260/112 B |

FOREIGN PATENT DOCUMENTS

| | | |
|---|---|---|
| 1,949,314 | 4/1970 | Fed. Rep. of Germany. |
| 2,029,455 | 2/1971 | Fed. Rep. of Germany. |
| 1,178,958 | 1/1970 | United Kingdom. |

OTHER PUBLICATIONS

Chem. Abstracts, vol. 55, 1961, 27584g, Engelberg.
Am. J. of the Medical Sciences, 1965, pp. 643–650, Webster et al.
Circulation, vol. XXIII, 1961, pp. 578–581, Engelberg.
Nature, vol. 203, 1964, Pool, p. 312.
Dictionary of Organic Compounds, Fourth Ed., vol. 3, 1965, p. 1567.
Chem. Abstracts, vol. 56, 1962, 7847i, Mayer et al.
Chem. Abstracts, vol. 78, 55900j, Wilms, 1971.
Thrombosis et al., Diathesis Haemorrhagica, vol. XI, pp. 64–74, (1964), Wagner et al.
Human Blood Coagulation, Biggs, (1972), pp. 142–147, 272–285.
"Plasma Transfusions in Hemophilia," Van Creveld et al., 1952.
Circulation Res., vol. 3, pp. 397–402, (1955), Monkhouse et al.
. . . Klinische Medizin, J. Tagung der Sektion Inner Medizin . . . 10, bis 13, Oct. 1963, pp. 311–317, (English).
Blood Clotting Enzymology, Seegers, (1967), pp. 113–115, 170–177.
"The Hemophilias," Brinkhous, Wagner, et al., pp. 81–86, 100–105.
"Hemophilia and New Hemorrhagic States," Brinkhous. pp. 67–76.
Plenary Session Papers, XII Congress International Society of Hematology, 1968, pp. 315–320.
Am. J. of the Medical Sciences, vol. 232, 1956, pp. 434–441 Penick et al.
"Hemophilia and Other Hemorrhagic States," Brinkhous, pp. 38–46, Seegers et al.
Nature, vol. 184, 1959, p. 450, Miller.
Who Technical Report Series, 504, 1972, p. 19.
British 3, Haemat, vol. 13, pp. 42–52 (1967), Preston.
Preparation of Factor IX Concentrates . . . Josso et al., pp. 14–21.
Thromb. Diath. Haemorrh., vol. 9, pp. 368–386 (1963), Blomback et al.
Compt. Rend. Soc. Biol., 155 (1961), pp. 1103–1106, Mayer et al.
Thromb. Diath. Haemorrhagia, vol. 17, pp. 381–387 (1967) Kisker.
British J. of Haematology, vol. 21 (1971), pp. 1–20, Newman et al.
. . . Hamatologie Leipzif, 10–bis 13, 1963, pp. 311–317, Soulier et al.
Human Blood Coagulation, Denson et al., (1972), pp. 278–285.
Lancet, 1963, pp. 70–73, von Francken et al.
International Symposium, Brussels, 1976, pp. 27–29, 42–44, 50–60, Verstraete et al.
Proc. 7th Congr. Europ. Soc. Haemat., 1959, part II, pp. 587–593 (1960), Blomback et al.

*Primary Examiner*—Howard E. Schain

*Attorney, Agent, or Firm*—Paul C. Flattery; Lawrence W. Flynn; Max D. Hensley

[57] ABSTRACT

A method of improving the yield of antihemophilic Factor [A] *VIII (AHF)* obtained from blood plasma and plasma fractions *by cryoprecipitation* comprising the addition of from 0.01 to 10 units of heparin to *a concentrate of AHF obtained by cryoprecipitation from* said plasma or plasma fraction per ml. of solution thereof.

21 Claims, 1 Drawing Figure

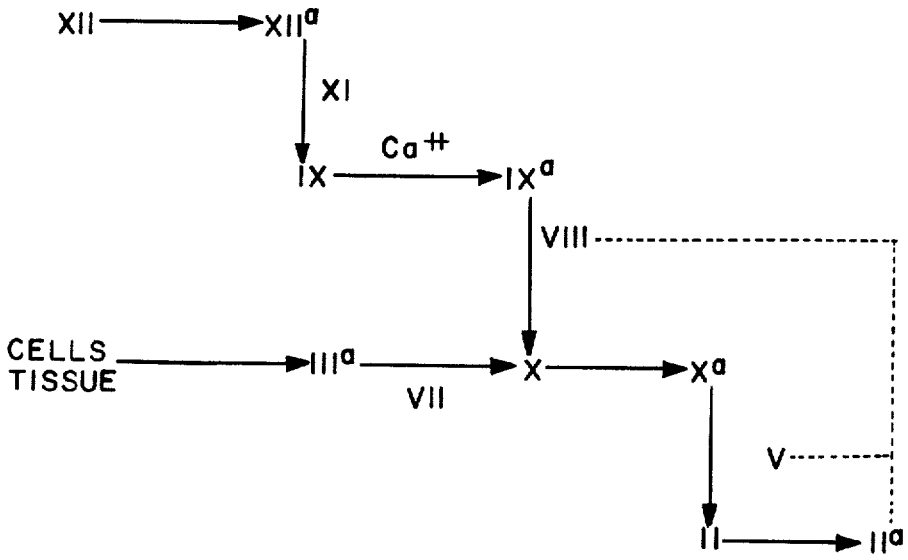
XII
XIIa
XI
IX
Ca++
IXa
VIII
CELLS
TISSUE
IIIa
VII
X
Xa
V
II
IIa

STABILIZATION OF AHF USING HEPARIN

Matter enclosed in heavy brackets [ ] appears in the original patent but forms no part of this reissue specification; matter printed in italics indicates the additions made by reissue.

This invention relates to a method of making a concentrate of Antihemophilic Factor (AHF, Factor VIII). More particularly, this invention relates to a method for improving the yield of AHF obtained from blood plasma and plasma fractions *by a cryoprecipitation technique.*

The process of blood coagulation is a complicated biological activity and involves the interaction of several substances found in normal whole blood. It is known that certain factors associated with the blood coagulation mechanism are absent or seriously deficient in certain individuals. Thus, it is known that classical hemophilia (hemophilia A) is a deficiency disease caused by the absence of AHF (Factor VIII). In individuals suffering from the congential hemophilia known as hemophilia B, the blood is deficient in plasma thromboplastin component (PTC, Factor IX). Several other factors which are important in the coagulation mechanism are Factors II, VII and X.

Until recent years, treatment of hemophiliacs consisted of transfusing the patient with whole blood or blood plasma. Better medical practice dictates that, whenever possible, the patient be administered only those blood components in which he is deficient. Due to the universal shortage of blood, it is also advantageous to fractionate blood into its various components, whereby they can be used for patient treatment as required.

Various methods of fractionating blood and blood plasma into its separate components or concentrates thereof are known. The work of Edwin Cohn and his associates at Harvard University in the development of the alcohol fractionation method is particularly noteworthy. With specific reference to the production of AHF, recent U.S. Pats. [3,631,078] *3,361,018* and 3,652,530 illustrate improved methods of obtaining a highly purified concentrate of that factor.

In the investigational work of Wagner, Thelin, Brinkhouse and others interested in the production of AHF, it was found that the presence of prothrombin (Factor II) and its associated complex of factors was detrimental to the stability of Factor VIII, both long term and short term. The usual treatment to obviate this problem was the removal of the prothrombin complex with various agents such as aluminum hydroxide, magnesium hydroxide, barium carbonate, barium sulfate, rivanol (6,9-diamino 2-ethoxyacridine lactate), IRC-50 ion exchange resin (XE-64-Rivanol) and glycine ethyl ester.

While the foregoing agents are generally effective, various serious drawbacks to their use in clinical applications have become apparent. Factor VIII is indeed stabilized by use of these agents since the removal of prothrombin does not allow for thrombin generation. Thrombin is chiefly responsible for the degradation of Factor VIII, as reported by Kisker, Thromb, Diath. Haemorrhagica, vol. 17, p. 381 (1967) and Penick and Brinkhous, Amer. J. Med. Sciences, vol. 232, p. 434 (1956). Thus, in the preparation of Factor VIII with aliphatic amino acids, the original work by Wagner et al. employed aluminum hydroxide to (1) decrease degradation of Factor VIII while concentrating manipulations were being employed, and (2) increase the long term stability, both after lyophilization and reconstitution. The Hemophilias, K. M. Brinkhous, Ed., International Symposium, Washington, D.C., Univ. of North Carolina Press, p. 81 (1964). However, the inclusion of trace amounts of aluminum was considered clinically unsafe.

The advent of cryoprecipitation and the one step production of relatively high potency concentrates appeared to obviate the use of any means of removing the prothrombin complex. Pool et al., Nature, vol. 203, p. 312 (1964). However, it has been found in practice that high variability existed in yields of AHF, up to and even exceeding 50% variability of the mean values reported.

Accordingly, it is an object of this invention to provide an improved method of making a *cryoprecipitate* concentrate of Antihemophilic Factor (AHF, Factor VIII).

It is another object of this invention to provide a method for improving the yield of AHF *concentrates* obtained *by cryoprecipitation* from blood plasma and plasma fractions.

Other objects and advantages of the present invention will be apparent to those skilled in the art after reading the disclosure hereof.

In brief, the present invention resides in the addition of heparin to [the aqueous media containing the] *an AHF concentrate obtained from* blood plasma or *a* plasma fraction *by cryoprecipitation,* which [is] *may* then *be further* fractionated to obtain [a concentrate] *an even more concentrated form* of AHF.

*Preferably, the heparin is added to the AHF-rich concentrate in addition to citrate. A preferred method of conducting this double anticoagulant addition is to add the heparin to the cryoprecipitate in the form of a heparinized, citrated saline solution. When the AHF-rich cryoprecipitate is further fractionated to obtain a high purity, more concentrated form of AHF, heparin is preferably added twice, once to the initial cryoprecipitate and subsequently to the further fractionated AHF concentrate. In each case, heparin is preferably added along with a citrate as a second anticoagulant.*

It is believed that the invention will be better understood by reference to the accompanying drawing. The FIGURE in the drawing presents a diagram which represents the blood clotting mechanism. The roman numerals represent the several blood clotting factors. It will be understood, however, that this diagram represents only a working hypothesis based on present knowledge, and the inventors do not intend to be limited or bound by this hypothesis.

As has been stated above, high variability in the yield of AHF has been obtained in practice in the production of AHF *by cryoprecipitation.* The longer the manipulations in concentration take, the lower the yield of AHF. The losses in yield have been somewhat ameliorated by scrupulous attention to the removal of blood cells. These results may be explained by reference to the clotting diagram of the accompanying drawing. Of particular interest is the feedback mechanism shown by the dotted lines, which indicate the action of Factor IIα (thrombin) on Factor V (proaccelerin), and Factor VII (AHF). The action consists of two parts: the actions of VIII and V are (1) first enhanced by altered tertiary structure and then (2) degraded to stop excessive clotting, which could lead to circulatory embarrassment.

It is apparent, from the clotting diagram, that the removal of Factors II, VII, X and IX (prothrombin complex) would eliminate the feedback mechanism since there would be no II to produce IIα. The observation, by the present inventors, that cell free plasma allows concentration to proceed with higher yields of AHF being produced also is explainable by the clotting diagram, since thromboplastin is not produced and, therefore, the beginning of clotting cannot start.

In accordance with the present invention, it has now been found that the yield of AHF *obtained by cryoprecipitation* in production size amounts can be enhanced by the addition of heparin during the fractionation. It has been observed, by the inventors, that in contrast to prior practice without the use of heparin, when the heparin is employed (1) cell contamination, such as from the fractionation procedure, does not lead to lower yields, (2) tissue contamination, such as occurs during intravenous administration, does not produce lower yields, (3) longer processing time does not reduce the yield, and (4) reconstituted stability is increased over non-heparinized plasma concentrates by at least an order of 30 times. Thus, it unnecessary in the practice of this invention to remove the prothrombin complex to achieve stability of Factor VIII concentrates and the usual losses in yield from cell and tissue contamination or extended processing times are overcome.

The amount of heparin employed in the practice of this invention during the fractionation of AHF can vary within reasonable limits. It has been found that a concentration of about one unit of heparin per ml. of the plasma solution or plasma fraction is about optimum. Concentrations greater than about 10 units per ml. are to be avoided as unnecessary and dangerous. Concentrations of about 0.01 unit per ml. are also effective. The preferred range is from about 0.01 to about 10 units per ml. One unit of heparin is defined herein to mean one U.S.P. (United States Pharmacopoeia) unit. The U.S.P. unit of heparin is the quantity that will prevent 1.0 ml. of citrated sheep plasma from clotting for one hour after the addition of 0.2 ml. of a 1:100 $CaCl_2$ solution. As used herein, the term "heparin" also is meant to include the sodium salt of heparin, the latter substance being preferred due to its water solubility.

The invention defined herein has been found useful in various procedures for producing AHF concentrates [and is applicable to any plasma or plasma fraction which contains AHF in admixture with any of the prothrombin complex factors.] *by cryoprecipitation.* Thus, it has been adapted to methods of fractionating AHF (1) from plasma *or plasma fractions* by [glycine precipitation] *cryoprecipitation*, (2) from cryoprecipitate by glycine precipitation, (3) from cryoprecipitate by polyethylene glycol precipitation, (4) from cryoprecipitate by polyethylene glycol and glycine precipitation, (5) from cryoprecipitate, [(6) from plasma,] and [(7)] *(6)* from cryoprecipitate by polyethylene glycol and glycine precipitation followed by "Ecteola" chromatography.

A preferred method of producing AHF to which the present invention is adapted is the method described in U.S. Pat. No. 3,631,018, whereby polyethylene glycol (PEG) and glycine are used to fractionate a cryoprecipitate of AHF concentrate. Thus, in Example 4 of said patent, at the step wherein the crypoprecipitate is dissolved in glycine citrated saline, about one unit of heparin is added per ml. of the solution. Following the precipitation with polyethylene glycol at 10% concentration, the redissolved precipitate is again treated to contain about one unit of heparin per ml. of the solution due to the loss of heparin during the fractionation with 10% polyethylene glycol. The heparin can conveniently be added by incorporation in the citrated saline or glycine citrated saline used to dissolve the respective precipitates.

The following examples will further illustrate the present invention, although it will be understood that the invention is not limited to these specific examples.

EXAMPLE 1

A stable human AHF concentrate of high potency and in high yield is produced in the following manner:

Reagents

Citrated saline.—One part 0.1 molar sodium citrate to four parts by weight 0.9 percent saline.

Glycine citrated saline.—Sufficient glycine is added to the above prepared citrated saline to make a 0.1 molar solution respective of glycine.

Buffered wash water.—To distilled water is added 1/100 volume of buffered citrate which is prepared by adjusting 0.5 molar sodium citrate with 0.5 molar citric acid to pH 6.88.

Heparin.—U.S. Pharmacopoeia grade material is used ("Lipo-Hepin"-sodium heparin injection, aqueous).

Acetic acid.—Prepared in both 1.0 normal and 0.1 normal aqueous solutions.

Glycine.—Prepared in both 1.3 and 1.8 molar aqueous solutions.

Procedure

Human blood plasma is received frozen (at below 4° C.) from a donor center. The plasma is pooled into Pfaudler kettles and, while held at a [temperature at 20° C. to −40° C.,] *temperature sufficient to produce a cryoprecipitate containing AHF,* it is centrifuged by continuous flow or bucket centrifugation *to recover the cryoprecipitate.* To the cryoprecipitate, glycine citrated saline solution containing one unit of heparin per ml. is added, the amount being one-tenth the volume of plasma the cryoprecipitate represents. Dissolution is brought about by mixing the cryoprecipitate and glycine citrated saline solution in a warm environment (normal room temperature, but not in excess of 30° C.).

The dissolved cryoprecipitate is adjusted to pH 6.5 with 0.1 normal acetic acid. Polyethylene glycol 4000 (molecular weight average about 4000) is added to the solution to make the PEG concentration about 3.5 percent. The mixture is gently agitated at room temperature for ten minutes and then centrifuged for fifteen minutes at 5000 r.p.m. The supernate is decanted and adjusted to pH 6.88 with 0.1 normal sodium hydroxide. Additional PEG 4000 is added to the solution to make the final PEG concentration about 10 percent. The mixture is gently agitated at room temperature for thirty minutes and centrifuged at 5000 r.p.m. for one-half hour. The supernate is decanted and discarded. The precipitate is washed in cold water (2° C.) and spin washing is then carried out for five minutes at 5000 r.p.m. at a temperature of −4° C. The supernate is decanted and the precipitate is redissolved in glycine citrated saline solution containing one unit of heparin per ml. Again, the amount of the redissolving solution is about one-tenth the volume of plasma that the precipitate represents.

The redissolved precipitate is adjusted to pH 6.88 with 0.1 normal acetic acid and reprecipitated with aqueous glycine having a molarity of 1.8. Sufficient glycine is added during this precipitation step to make the mixture 1.8 molal with respect to glycine. The mixture is gently agitated for 45 to 60 minutes at a temperature of from 2° C. to 10° C., and then centrifuged by continuous flow or bucket centrifugation. The resulting precipitate is collected and gently washed with buffered wash water and redissolved in citrated saline. The solution is clarified by filtration using a 293 mm. millipore filter (membranes used: 1.2 microns, 0.45 micron, and 0.3 micron).

The liquid product is then frozen by shell freezing (−60° C.) and storing in a flash freezer (−20° C. to −30° C.) for at least three hours.

The foregoing procedure was repeated except that no heparin was added to the glycine citrated saline used to dissolve the initial cryoprecipitate or to dissolve the dissolve from the fractionation with 10% PEG or at any other point in the fractionation.

The foregoing procedures, both with and without the addition of heparin, were both repeated.

The following table sets forth the results in these four fractionation runs:

| | AHF YIELD | | | |
|---|---|---|---|---|
| Procedure used | Cryo yield, percent AHF recovered from starting plasma | Final product yield AHF, percent recovered from starting plasma | Percent recovery, percent recovered from cryo. step | Total volume of starting plasma, liters |
| Without heparin | 35 | 13.6 | 38 | 6,000 |
| With heparin | 35 | 17 | 49 | 300 |
| Without heparin | 32 | 12.5 | 39 | 6,000 |
| With heparin | 33 | 17 | 52 | 300 |

In the table, it is seen that the final AHF yield when heparin was employed was 17%, whereas the yield without heparin averaged from 12.5% to 13.6%. The addition of heparin, therefore, increased the yield by 25% to 35% over the non-heparinized procedure. When the final AHF yield is divided by the cryoprecipitate AHF yield, it is seen that the efficiency of the process was improved from 38% and 39% without the heparin addition to 49% and 52% with the heparin addition.

When PEG 6000 is substituted for an equivalent amount of PEG 4000, in the above example, substantially similar results are obtained.

EXAMPLE 2

The procedure of Example 1 was repeated up to the step of [resuspending] *suspending* the initial cryoprecipitate in glycine citrated saline both with and without heparin in the solution. The final AHF yield in these two cryoprecipitate concentrates of AHF was 34% when heparin was not employed and 41% when heparin was used. This is equivalent to a 21% improvement in yield.

EXAMPLE 3

The procedure of Example 2 was repeated except that the cryoprecipitate concentrates, both with and without heparin, were lyophilized and then reconstituted with water and allowed to stand at room temperature (ca. 25° C.) for 24 hours. The heparinized sample retained 98% of the initial AHF activity prior to the standing period whereas the non-heparinized sample retained only 72% of the initial AHF activity.

Various other examples and modifications of the foregoing examples will be apparent to the person skilled in the art after reading the foregoing specification and the appended claims without departing from the spirit and scope of the invention. All such further examples and modifications are included within the scope of the appended claims.

What is claimed is:

1. The method of improving the yield of AHF obtained from blood plasma and plasma fractions comprising admixing from about 0.01 to about ten units of heparin to a concentrate of AHF obtained from said plasma or plasma fraction by cyroprecipitate per ml. of solution of said concentrate of AHF.

2. The method of claim 1 in which the plasma fraction is a cryoprecipitate concentrate of AHF which is further fractionated with both polyethylene glycol and glycine.

3. The method of claim 2 in which the polyethylene glycol has an average molecular weight of about 4000.

4. The method of claim 2 in which the cryoprecipitate concentrate is precipitated with from about 3% to about 4% polyethylene glycol, the resulting supernant is precipitated with about 10% polyethylene glycol, and the resulting supernate is then fractionated with glycine.

5. The method of claim 4 in which the polyethylene glycol has an average molecular weight of about 4000.

6. The method of claim 4 in which the glycine has a molarity of about 1.8.

7. The method of claim 4 in which the polyethylene glycol has an average molecular weight of about 4000 and the glycine has a molarity of about 1.8.

*8. The method of claim 1 wherein citrate in addition to heparin is admixed with said concentrate of AHF.*

*9. The method of claim 1 wherein the heparin admixed with said concentrate of AHF is a citrate solution of heparin.*

*10. The method of claim 1 further including the steps of fractionating the concentrate of AHF with which the heparin is admixed to increase the concentration of AHF, and admixing additional heparin with the further fractionated concentrate of AHF.*

*11. The method of claim 10 wherein citrate in addition to heparin is admixed with said further fractionated concentrate of AHF.*

*12. The method of claim 11 wherein the additional heparin admixed with said further fractionated concentrate of AHF is a citrate solution of heparin.*

*13. The method of improving the yield of AHF comprising the addition of heparin and a citrate to a concentrate of AHF obtained from plasma or a plasma fraction by cryoprecipitation, said heparin being added in an amount of about 0.01 to about 10 units per ml. of solution of said concentrate of AHF.*

*14. The method of claim 13 wherein about 1 to 10 units of heparin is added per ml. of solution of said concentrate of AHF.*

*15. The method of claim 13 wherein the heparin containing concentrate of AHF is further fractionated to increase the concentration of the AHF, and additional heparin and citrate are added to the further fractionated concentrate of AHF.*

*16. The method of improving the yield of AHF obtained from an AHF-rich cryoprecipitate comprising forming a solution of said cryoprecipitate and providing in said solution from an external source heparin and citrate, said heparin being added in an amount of about 0.01 to about 10 units per ml. of solution of said cryoprecipitate.*

*17. The method of claim 16 wherein said solution is provided from an external source with about 1 to 10 units of heparin per ml.*

*18. The method of improving the yield of an AHF concentrate prepared from plasma and plasma fractions comprising:*

*separating an AHF-rich cryoprecipitate from blood plasma or a blood plasma fraction;*

*adding heparin and citrate to the cryoprecipitate, said heparin being added in an amount of about 0.01 to about 10 units per ml. of solution of said cryoprecipitate;*

*fractionating the heparin containing AHF cryoprecipitate with polyethylene glycol to further concentrate the AHF; and*

*adding heparin and citrate to the further concentrated AHF, said heparin being added in an amount of about 0.01 to about 10 units per ml. of solution of said further concentrated AHF.*

*19. The method of claim 18 wherein the heparin-treated, further concentrated AHF is fractionated with glycine.*

*20. The method of improving the yield of an AHF concentrate obtained from plasma by cryoprecipitation, comprising forming a solution of said concentrate of AHF and providing in said solution about 0.01 to about 10 units of externally added heparin per ml. of solution.*

*21. The method of claim 20 further including the step of providing in said solution a citrate.*

* * * * *

UNITED STATES PATENT AND TRADEMARK OFFICE

CERTIFICATE OF CORRECTION

PATENT NO. : Reissue 29,698

DATED : July 11, 1978

INVENTOR(S) : Lajos F. Fekete and Stephen L. Holst

It is certified that error appears in the above-identified patent and that said Letters Patent are hereby corrected as shown below:

Page 1, item [54], "STABILIZATION OF AHF USING HEPARIN" should read -- AHF YIELDS USING HEPARIN--.

Page 1, right hand column, (OTHER PUBLICATIONS), "British 3, Haemat, vol. 13, pp. 42-52 (1967), Preston" should read --British J. Haemat., vol. 13, pp. 42-52 (1967), Preston--, and "International Symposium, Brussels, 1976, pp. 27-29, 42-44, 50-60, Verstraete et al" should read --Conference on Cryoprecipitated Factor VIII, International Symposium, Brussels, 1967, pp. 27-29, 42-44, 50-60, Verstraete et al--.

Column 1, line 2, "STABILIZATION OF AHF USING HEPARIN" should read -- AHF YIELDS USING HEPARIN--.

Column 1, line 24, "congential" should read --congenital--.

Column 1, line 44, "3,361,018" should read --3,631,018--.

UNITED STATES PATENT AND TRADEMARK OFFICE

CERTIFICATE OF CORRECTION

PATENT NO. : Reissue 29,698

DATED : July 11, 1978

INVENTOR(S) : Lajos F. Fekete and Stephen L. Holst

It is certified that error appears in the above-identified patent and that said Letters Patent are hereby corrected as shown below:

Column 2, line 66, "VII" should read --VIII--.

Column 5, line 21, "dis-" and column 5, line 22, "solve" should read --precipitate--.

Column 6, line 17, "cryoprecipitate" should read --cryoprecipitation--.

Signed and Sealed this

*Nineteenth* Day of *June 1979*

[SEAL]

*Attest:*

RUTH C. MASON
*Attesting Officer*

DONALD W. BANNER
*Commissioner of Patents and Trademarks*